United States Patent [19]

Salek et al.

[11] Patent Number: 5,146,012
[45] Date of Patent: * Sep. 8, 1992

[54] MANUFACTURE OF NEOPENTYL GLYCOL (III)

[75] Inventors: Jeffrey S. Salek, Oakdale Boro; Joseph Pugach, Monroeville Boro; Carole L. Elias, Allegheny County; Leonard A. Cullo, Greensburg, all of Pa.

[73] Assignee: Aristech Chemical Corporation, Pittsburgh, Pa.

[*] Notice: The portion of the term of this patent subsequent to Sep. 1, 2009 has been disclaimed.

[21] Appl. No.: 723,097

[22] Filed: Jun. 28, 1991

Related U.S. Application Data

[63] Continuation-in-part of Ser. No. 691,927, Apr. 26, 1991, and Ser. No. 716,177, Jun. 17, 1991.

[51] Int. Cl.$^5$ .................... C07C 29/14; C07C 31/20; C07C 45/45
[52] U.S. Cl. ................... 568/881; 568/853; 568/880; 568/457; 568/463; 568/464; 568/458
[58] Field of Search ............. 568/853, 881, 457, 458, 568/463, 464, 880

[56] References Cited

U.S. PATENT DOCUMENTS

| | | | |
|---|---|---|---|
| 2,135,063 | 11/1938 | Walker et al. | 260/635 |
| 2,317,456 | 4/1943 | Hanford et al. | 260/602 |
| 2,778,858 | 1/1957 | Meinhofer | 260/635 |
| 2,786,083 | 3/1957 | Wyler | 260/635 |
| 2,811,562 | 10/1957 | Hagemeyer, Jr. | 260/602 |
| 3,340,312 | 9/1967 | Duke, Jr. et al. | 260/635 |
| 3,504,042 | 3/1970 | Shimono et al. | 260/635 |
| 3,808,280 | 4/1974 | Merger et al. | 260/635 A |
| 3,876,706 | 4/1975 | Levanevsky et al. | 260/602 |
| 3,920,760 | 11/1975 | Heinz | 260/635 A |
| 3,935,274 | 1/1976 | Jacobsen et al. | 260/602 |
| 3,975,450 | 8/1976 | Palmer et al. | 260/635 P |
| 4,094,914 | 6/1978 | Rottig et al. | 568/862 |
| 4,219,508 | 8/1980 | Wagner | 568/463 |
| 4,250,337 | 2/1981 | zur Hausen et al. | 568/853 |
| 4,851,592 | 7/1989 | Morris | 568/853 |
| 4,855,515 | 8/1989 | Morris et al. | 568/862 |
| 4,933,473 | 6/1990 | Ninomiya et al. | 568/862 |
| 4,945,184 | 7/1990 | Pugach et al. | 568/313 |

FOREIGN PATENT DOCUMENTS 1017618 1/1966 United Kingdom.

Primary Examiner—Marianne M. Cintins
Assistant Examiner—Rebecca Cook
Attorney, Agent, or Firm—William L. Krayer

[57] ABSTRACT

Neopentyl glycol is made from isobutyraldehyde and paraformaldehyde; the aldol reaction product is directly mixed with a lower alcohol for hydrogenolysis.

12 Claims, No Drawings

MANUFACTURE OF NEOPENTYL GLYCOL (III)

RELATED APPLICATIONS

This application is a continuation-in-part of U.S. Ser. No. 691,927, filed Apr. 26, 1991, entitled "Manufacture of Neopentyl Glycol (I)" and Ser. No. 716,177, filed Jun. 17, 1991, entitled "Manufacture of Neopentyl Glycol (II)" by two of the inventors herein.

TECHNICAL FIELD

This invention relates to the manufacture of neopentyl glycol (NPG) from isobutyraldehyde and formaldehyde; in particular, it employs formaldehyde preferably in the form of paraformaldehyde, and is restricted to the use of certain specified steps and conditions in the hydrogenation of the product of the reaction of formaldehyde and isobutyraldehyde (IBAL).

BACKGROUND ART

In the above-referenced parent patent applications, paraformaldehyde is used to react with isobutyraldehyde to make a product comprising in the case of U.S. Ser. No. 691,927, hydroxypivaldehyde (HPA), and in U.S. Ser. No. 716,177, 3-hydroxy-2,2-dimethylpropylhydroxypivalate. The products are hydrogenated to make NPG. The two applications describe different catalyst systems for the aldol reaction; the hydrogenation step is distinguished primarily by the fact that the feed material for it, i.e. the reaction product of the aldol step, after dissolution in a suitable alcohol, may be fed directly to the hydrogenation step. This is due to the use of paraformaldehyde as the formaldehyde reactant, which greatly reduces the presence of water and avoids other complications. The present application is an improvement of both inventions, and in the manufacture of NPG generally, in that the present application recognizes the unique composition of the aldol reaction product made using paraformaldehyde and optimizes the hydrogenation process for it, i.e. for any aldol process utilizing paraformaldehyde. In the present invention, the aldol reaction is not limited to the use of the catalysts described in the parent applications, but embraces any reaction of IBAL and paraformaldehyde; moreover, the hydrogenolysis process of the present invention is applicable to aldol reaction products made with aqueous formaldehyde where the water is substantially removed from the aldol reaction product.

While the present application is limited to the hydrogenation and/or hydrogenolysis of substantially water-free reaction products of IBAL and formaldehyde, preferably paraformaldehyde, certain prior art may be considered relevant wherein HPA or other product obtained from the reaction of IBAL and aqueous formaldehyde is converted to NPG through hydrogenation; such references include those employing copper chromite hydrogenation catalysts, for example. References which employ copper chromite and other hydrogenation catalysts with the conventional aqueous formaldehyde system may be exemplified by U.S. Pat. No. 4,855,515, which recites the historical development of the reaction and emphasizes the use of a particular catalyst in the hydrogenation step. U.S. Pat. No. 3,808,280 discloses the use of triethylamine as a catalyst for the (aqueous) formaldehyde/isobutyraldehyde reaction.

Each of the above references employs formaldehyde in the form of aqueous formaldehyde.

Paraformaldehyde is used by Snam S.p.A. in UK Patent No. 1,017,618 to react with IBAL in the presence of a tertiary amine to produce a reaction product containing apparently predominantly HPA which may be hydrogenated to NPG. However, the instant invention teaches the addition of a suitable alcohol solvent prior to hydrogenation which produces a high purity NPG product by simple distillation, obviating the need for additional expensive purification steps.

While zur Hausen et. al., U.S. Pat. No. 4,250,337 may use the aldol reaction product directly in their hydrogenation step, they also teach the use of small amounts of water, in contrast to the process of the present invention, which advantageously uses an alcohol in the hydrogenolysis step. As a result, our invention achieves high NPG purities together with high yields unlike the aforementioned patent which can only achieve equivalent purities at uneconomical yields.

Other prior art processes which emphasize the hydrogenation step include U.S. Pat. Nos. 4,094,914 to Rottig et. al. and 4,933,473 to Ninomiya et al. Ninomiya et al. especially recognize the formation of the HPA dimer in the aldol reaction product. While Rottig et al. use alcohols in a vapor phase hydrogenation, they do not employ paraformaldehyde in the aldol step as applicants do nor do they recognize or demonstrate ester hydrogenolysis.

SUMMARY OF THE INVENTION

In the present invention, paraformaldehyde and IBAL are reacted, with or without the presence of certain recited catalysts, to make a reaction product which is passed directly to a hydrogenation step including the addition of an alcohol of the formula RR'CHOH wherein R and R' are independently selected from hydrogen and alkyl groups having from 1 to 5 carbon atoms, and the thus dissolved product is passed over a suitable hydrogenation catalyst at a pressure of at least 500 psig to about 3000 psig and a temperature of about 100° C. to about 200° C. to recover an NPG product of at least 99% purity by simple distillation. We prefer to use a hydrogenolysis feed containing about 40% to about 90% alcohol; the preferred alcohol is methanol.

Our invention will be described in detail in connection with the examples to follow.

DETAILED DESCRIPTION OF THE INVENTION

In the discussion below, it is important to keep in mind the basics of the reactions discussed. First is the aldol reaction:

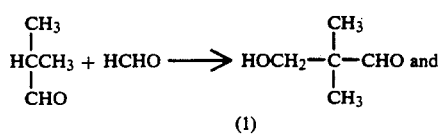

(1)

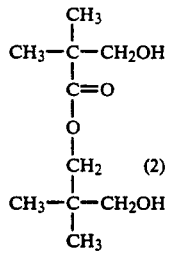

Product (1), which is the major product, is HPA. Product (2) corresponds to 3-hydroxy-2,2-dimethylpropyl-hydroxypivalate, which will be referred to herein as "HNHP", which stands for hydroxyneopentylhydroxypivalate. HNHP is generally a minor product made by the Tishchenko reaction of HPA. In the presence of an appropriate catalyst, pressure, heat and hydrogen, the reaction product including both HPA and HNHP is hydrogenated to form NPG:

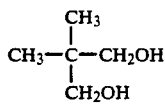

The conventional aqueous processes for making NPG by the above route have the disadvantages of significant wastewater quantities, a significant incidence of ester and acid impurities not readily separable from NPG and which must be saponified and neutralized, creating another waste stream, an extraneous extraction step on the waste stream to increase efficiency, and a relatively expensive purification step. By using the process of our invention, with or without paraformaldehyde, rather than the prior art formaldehyde process, the just-recited disadvantages are obviated. Our process not only avoids these disadvantages but also conducts the hydrogenation step with much greater efficiency. The purity of the NPG product obtained by simple distillation following the teachings of this invention is higher than that obtained by prior art.

The process taught by the instant invention is much more environmentally friendly than prior art aqueous processes. The volume of wastewater discharged by our process is approximately 80% less than seen in conventional aqueous processes.

Additionally, it has been demonstrated, as will be described herein, that generation of HPA using paraformaldehyde followed by catalytic hydrogenation in an alcoholic solvent can be performed under conditions of hydrogenolysis so that ester impurities are reduced to their corresponding alcohols. NPG product can be obtained from the reduced effluents at >99.5% purity by simple distillation in yields at least comparable to the conventional NPG process using aqueous formaldehyde.

The high NPG purity of the hydrogenated aldol effluent makes it feasible to eliminate three processing steps: caustic treatment, a distillation or evaporation step such as wiped-film evaporation, and IBAL extraction (see U.S. Pat. No. 4,935,555 to Elias et. al.). We have produced NPG product in purities greater than 99.5% using this simplified processing scheme. Finally, we have demonstrated to our great surprise that high NPG purities can be achieved at hydrogenation pressures as low as 500 psig $H_2$.

The present invention includes as an initial step the method of making HPA, and particularly its dimer, 2-[1,1-dimethyl-2-hydroxymethyl]-5,5-dimethyl-4-hydroxy-1,3-dioxane, and subsequently NPG, by reacting IBAL with paraformaldehyde in the presence of a tertiary amine catalyst alone or in combination with one or more oxides of elements of Groups IB, IVA, IVB, VA, VB, VIB and VIII of the periodic table (Chemical Rubber Company Handbook) to obtain HPA and HPA dimer. The HPA and its dimer are hydrogenated by the process disclosed herein to obtain NPG.

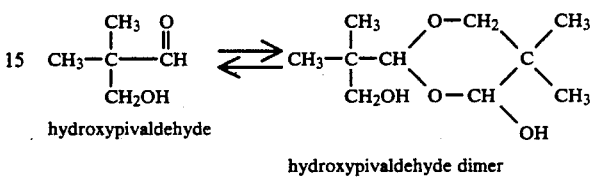

hydroxypivaldehyde     hydroxypivaldehyde dimer

In the presence of the metal oxide, HPA is obtained at a faster rate and with a higher yield. Whether or not the HPA or its dimer is isolated and/or purified, they are conveniently hydrogenated in the form of a methanol (or other alcohol as described elsewhere herein) solution, and in the presence of a copper chromite catalyst, for example, to obtain the desired neopentyl glycol. The HPA dimer hydrogenates as readily as HPA itself.

A specific reaction may be described as follows: The reaction is performed in a reflux apparatus wherein one equivalent of IBAL, one equivalent of paraformaldehyde, 0.01 equivalent of titanium dioxide, and about 0.04 to 0.05 equivalent of triethylamine have been placed under an inert atmosphere. The reaction mixture is stirred at the reflux temperature of IBAL (about 63°–64° C.) until the IBAL no longer refluxes, i.e. is consumed. The clear faintly yellow molten liquid obtained is decanted—or filtered from the titanium dioxide and gradually cooled to room temperature. HPA dimer can be obtained by allowing it to precipitate and then washing to remove the amine catalyst, or crystallizing from a methanol solution. The HPA dimer, together with any residual HPA, is hydrogenated by passing a methanol solution of the HPA-containing material over a copper chromite catalyst at about 160° C. and about 1000 psi, to obtain the NPG by simple distillation.

More generally, with one equivalent of IBAL we may place in a reaction vessel from about 0.5 to about 2 equivalents of paraformaldehyde, about 0.001 to about 0.1 (preferably about 0.005 to about 0.05) equivalent of one or more oxides of elements of Groups IB, IVA, IVB, VA, VB, VIB and VIII of the periodic table and about 0.01 to about 0.1 (preferably 0.02 to about 0.08) equivalent of a tertiary amine. The reaction mixture is stirred until reflux of the IBAL ceases. The resulting HPA and its dimer may be hydrogenated by the hydrogenolysis steps recited herein with or without further purification.

As is known in the art, if the amine chosen has a boiling point lower than the boiling point (reflux temperature) of IBAL, pressure may be necessary.

Our invention provides a process in which only minimal water is present and is therefore relatively easier to perform since it greatly reduces the separation requirements and disposal of wastewater; the process is also considerably more efficient than prior art processes, since the HPA product can be used directly, i.e. without an arduous separation or purification process, for the hydrogenation step to NPG. The process is also more efficient in that fewer by-products are made, a high yield is obtained at a faster rate, and indeed one need not be concerned with the complications of by-products. Paraformaldehyde is easier and safer to store under properly controlled conditions than aqueous formaldehyde, as well as resulting in lower emissions.

The metal oxide catalyst can be removed from the HPA reaction product before it is hydrogenated, by filtration or by any convenient means for recycling. The reaction may also be performed over a bed of catalyst.

We may use various tertiary amines. Specifically, we may use as catalysts any tertiary amines of the general formula $R^1R^2R^3N$ where $R^1$, $R^2$, and $R^3$ are independently selected from alkyl and aryl groups of the general formula $C_1$–$C_{15}$ and $R^1$ and $R^2$ may form a substituted or unsubstituted cyclic group having from about 5 to about 15 carbon atoms.

Following are several examples of the invention:

EXAMPLE 1

(A) 80 g of IBAL, 37.2 g of paraformaldehyde, and 5.6 g of triethylamine were charged with stirring into a 250 mL 3-neck roundbottom flask equipped with a reflux condenser, and stirbar. The apparatus was lowered into a heated oil bath (80° C.) and moderate IBAL reflux was observed within minutes. After 6h, the reaction was terminated, cooled to 60° C., then diluted in 400 g of methanol. The reaction effluent was charged to an autoclave together with 4.0 g of $CuCr_2O_4$ and hydrogenated for 1.5h at 150° C. and 1000 psig $H_2$.

(B) The aldol reaction followed by batch hydrogenation was repeated as described above except that 95.5 g of aqueous formaldehyde (37 wt. %) was used rather than paraformaldehyde. The batch hydrogenation was performed after diluting the reaction mixture in 400 g methanol using 4.0 g of $CuCr_2O_4$.

The results from the two experiments are compared and summarized in Table I. The results clearly demonstrate the differences in purity and yield of the conventional aqueous process and our paraformaldehyde process.

TABLE I

| Experiment | (A) | (B) |
|---|---|---|
| Formaldehyde Type | paraformaldehyde | aqueous |
| % Aldol/$CH_3OH$ | 20 | 20 |
| GC Analysis of Hydrogenated Effluent | | |
| % Isobutyl Alcohol | 5.43 | 10.40 |
| % Triethylamine | 5.68 | 6.44 |
| % Neopentyl Glycol | 84.08 | 67.12 |
| % Hydroxyneopentyl-hydroxypivalate | 3.28 | 4.82 |
| % Neopentyl Glycol Purity* | 98.39 | 96.35 |
| % Neopentyl Glycol Yield** | 97.54 | 85.35 |

*Neopentyl glycol purities calculated by GC on a "lights-free" (isobutyl alcohol, triethylamine and methanol), "hydroxyneopentylhydroxypivalate-free" basis.
**Neopentyl glycol yields were calculated from GC analyses of hydrogenated effluents.

EXAMPLE 3

(A) 80 g of IBAL, 37.2 g of paraformaldehyde, and 5.6 g of triethylamine were charged with stirring into a 250 mL 3-neck roundbottom flask equipped with reflux condenser, and stirbar. The apparatus was lowered into a heated oil bath (80° C.) and moderate IBAL reflux was observed within minutes. After 6h, the reaction was terminated, cooled to 60° C., then diluted in 400 g of methanol. The reaction effluent was charged to an autoclave together with 4 g of $CuCr_2O_4$ and hydrogenated for 1.5 h at 150° C. and 1000 psig $H_2$.

(B) 650 g of IBAL, 731.6 g of aqueous formaldehyde, and 41.5 g of triethylamine were charged with stirring into a 5L 3-neck roundbottom flask equipped with reflux condenser, and stirrer. The apparatus was lowered into a heated water bath (50° C.) which was gradually heated to a temperature of 80° C. and then maintained for 2.5 h. The reaction was then terminated and allowed to cool overnight. A white precipitate was recovered and dried. A portion of the recovered solid (90.2 g) was dissolved in 400 g of methanol. The methanolic solution was charged to an autoclave together with 4 g of $CuCr_2O_4$ and hydrogenated for 1.5 h at 150° C. and 1000 psig $H_2$.

The results from the two experiments are compared and summarized in Table III. These results demonstrate that aldol product made using aqueous formaldehyde or paraformaldehyde can be used to produce high purity NPG product in the hydrogenation/hydrogenolysis step providing the water is removed from the aqueous aldol and a suitable alcohol solvent is used to enhance hydrogenolysis as taught by this invention. Thus, the hydrogenation step described in this improved process would be applicable to an aldol effluent made using either aqueous formaldehyde or paraformaldehyde.

By a suitable alcohol solvent, we mean an alcohol of the formula $RR'CHOH$ wherein R and R' are independently selected from hydrogen and alkyl groups having from one to five carbon atoms. We prefer that the hydrogenolysis feed contain about 40% to about 90% alcohol. The alcohol can be recycled prior to recovering the neopentyl glycol.

TABLE III

| Experiment | (A) | (B) |
|---|---|---|
| Formaldehyde Type | paraformaldehyde | aqueous |
| % Aldol/$CH_3OH$ | 20 | 20 |
| GC Analysis of Hydrogenated Effluent | | |
| % Isobutyl Alcohol | 5.43 | 3.93 |
| % Triethylamine | 5.68 | 5.16 |
| % Neopentyl Glycol | 84.08 | 87.57 |
| % Hydroxyneopentyl-hydroxypivalate | 3.28 | 2.42 |
| % Neopentyl Glycol Purity* | 98.39 | 98.95 |
| % Neopentyl Glycol Yield** | 97.54 | 98.46 |

*Neopentyl glycol purities calculated by GC on a "lights-free" (isobutyl alcohol, triethylamine and methanol), "hydroxyneopentylhydroxypivalate-free" basis.
**Neopentyl glycol yields were calculated from GC analyses of hydrogenated effluents.

Table IV recites the results of experiments recited in parent patent application U.S. Ser. No. 691,927 with the addition of Example 16 utilizing

| Reagent | Equivalents |
|---|---|
| IBAL | 1.00 |
| Paraformaldehyde | 1.00 |
| Triethylamine | 0.050 |
| Metal oxide | 0.010 |

With the exception of Example 16, the reactions were terminated 1 hour after the IBAL stopped refluxing and then analyzed by G.C. Everything else was done as similarly as possible so that the effect of the metal oxides could be compared. HPA selectivity was calculated as the monomer.

TABLE IV

| Co-Catalyst | % IBAL Conv. | % HPA Sel. | % HNHP Sel. | Reaction Time (h) | Comments |
| --- | --- | --- | --- | --- | --- |
| 1. None | 92 | 92 | 3.7 | 2.42 | Control |
| 2. Nb$_2$O$_5$ | 97 | 96 | 1.3 | 2.08 | |
| 3. ZrO$_2$ | 98 | 97 | 1.0 | 2.00 | |
| 4. MnO$_2$ | 97 | 90 | 7.3 | 1.92 | |
| 5. As$_2$O$_3$ | 97 | 97 | 1.3 | 2.00 | |
| 6. CuO | 97 | 96 | 2.4 | 1.92 | |
| 7. TiO$_2$ | 99 | 98 | 0.3 | 1.17 | |
| 8. CdO | 97 | 66 | 29.0 | 1.08 | |
| 9. CeO$_2$ | 97 | 94 | 0.6 | 1.33 | |
| 10. NiO | 96 | 91 | 7.0 | 1.58 | |
| 11. Sm$_2$O$_3$ | 99 | 91 | 1.1 | 2.00 | |
| 12. Silica Gel | 97 | 97 | 1.7 | 2.50 | |
| 13. Cr$_2$O$_3$ | 99 | 95 | 2.7 | 1.58 | |
| 14. Bi$_2$O$_3$ | 99 | 96 | 2.1 | 2.50 | |
| 15. Y$_2$O$_3$ | 95 | 58 | 31.5 | 1.75 | |
| 16. Y$_2$O$_3$ | 99 | 10 | 67.6 | 6.0 | |

As may be seen from Table IV, the selectivity for HNHP was quite striking in the cases of cadmium oxide and yttrium oxide.

Our invention includes as a first step a method of making HNHP, by reacting IBAL with paraformaldehyde in the presence of a tertiary amine catalyst, preferably triethylamine, and an oxide selected from the group consisting of cadmium and yttrium oxide to obtain HNHP, as indicated in Experiments 8, 15 and 16 of Table IV. The HNHP/HPA mixture is thereafter hydrogenated by the steps disclosed herein to obtain NPG. The HNHP/HPA mixture may be isolated, typically in the form of a white solid. Whether or not the mixture is isolated, it is conveniently hydrogenated in the form of a methanol solution, in the presence of a copper chromite catalyst, for example, to obtain the desired neopentyl glycol.

A specific reaction may be described as follows: The reaction is performed in a reflux apparatus wherein one equivalent of IBAL, one equivalent of paraformaldehyde, 0.01 equivalent of cadmium oxide, and about 0.04 to 0.05 equivalent of triethylamine have been placed. The mixture is stirred at the reflux temperature of IBAL (about 63°–64° C.) for about one to three hours (or until the IBAL no longer refluxes, 2.5 to 3 or more hours i.e. is consumed). The clear yellow molten liquid obtained is decanted from the cadmium oxide and gradually cooled to room temperature. The HNHP/HPA mixture is hydrogenated in any conventional (convenient) manner such as by passing a methanol solution over a copper chromite catalyst at about 150° C. and about 2000 psi., to obtain the NPG, which is recovered by simple distillation.

EXAMPLE 4

Effect of stoichiometry on aldol condensation efficiencies

A batch reaction was performed at moderate IBAL reflux temperatures. Reactions were terminated 0.25 hours after IBAL reflux ceased. Reaction charge consisted of 0.050 equivalent of TEA relative to starting IBAL concentration and paraformaldehyde was varied as designated. Results are shown in Table IV.

TABLE IV

| RUN # | Condition | % Conversion (IBAL) | % Selectivity HPA | % Selectivity HNHP |
| --- | --- | --- | --- | --- |
| 1 | stoichiometric | 85–90% | 85–90% | 1–5% |
| 2 | 6% excess paraformaldehyde | 93% | 91% | 2.3% |
| 3 | 12% excess paraformaldehyde | >99% | 87–90% | 3–6% |

Isobutyraldehyde (2000.0 g, 27.74 mol), paraformaldehyde (929.3 g, 29.40 mol), and triethylamine (140.3 g, 1.39 mol) were charged with stirring into a 5L round-bottom flask fitted with a reflux condenser. The apparatus was lowered into a water bath (50° C.). The bath was heated to a temperature of 80° C. over a period of 1.5 h. The reaction was terminated (6 h) and the clear, faintly yellowish aldol effluent was diluted in methanol to make a 50 wt. % aldol in methanol solution. The hydrogenation was performed by passing the methanolic aldol effluent upward through a fixed-bed of CuCr$_2$O$_4$ at 160° C., 0.5 LHSV, and 1000 psig H$_2$ at >5:1 mole ratio H$_2$:HPA. The results are as shown:

| Components | Hydrogenated Solution (GC area %) | *Neopentyl Glycol Purity |
| --- | --- | --- |
| CH$_3$OH | 35.340 | |
| IBA | 1.697 | |
| IBacid | 0.000 | |
| TEA | 3.723 | |
| HPA | 0.000 | |
| NPG | 58.577 | 99.67% |
| esters | 0.194 | |
| HNHP | 0.424 | |

IBA = isobutyl alcohol
IBacid = isobutyric acid
TEA = triethylamine
HPA = hydroxypivaldehyde
NPG = neopentyl glycol
esters = e.g., neopentyl glycol monoformate, neopentyl glycol monoisobutyrate
HNHP = hydroxyneopentylhydroxypivalate
*NPG purities calculated by GC on a "lights-free" (CH$_3$OH, IBA, TEA), "HNHP-free" basis.

EXAMPLE 6

Hydrogenation was performed by passing methanolic aldol effluent (prepared as described in Example 5) upward through a fixed-bed of barium promoted CuCr$_2$O$_4$ at 160° C., 1000 psig H$_2$ at >5:1 mole ratio H$_2$:HPA, and 0.5 LHSV. Results follow:

| Components | Hydrogenated Solution (GC area %) | *Neopentyl Glycol Purity |
| --- | --- | --- |
| CH$_3$OH | 31.894 | |
| IBA | 2.149 | |
| IBacid | 0.004 | |
| TEA | 3.378 | |
| HPA | 0.007 | |
| NPG | 61.574 | **99.55% |
| esters | 0.277 | |
| HNHP | 0.455 | |

IBA = isobutyl alcohol
IBacid = isobutyric acid
TEA = triethylamine
HPA = hydroxypivaldehyde
NPG = neopentyl glycol
esters = e.g., neopentyl glycol monoformate, neopentyl glycol monoisobutyrate
HNHP = hydroxyneopentylhydroxypivalate
*NPG purities calculated by GC on a "lights-free" (CH$_3$OH, IBA, TEA), "HNHP-free" basis.
**A 10-tray fractional distillation gave 99.5+% NPG product purity.

EXAMPLE 7

Hydrogenation was performed by passing methanolic aldol effluent (prepared as described in Example 5) downward through a fixed-bed barium promoted $CuCr_2O_4$ at 160° C., 500 psig $H_2$ >5:1 mole ratio $H_2$:HPA, and 1.0 LHSV. Results follow:

| Components | Hydrogenated Solution (GC area %) | *Neopentyl Glycol Purity |
|---|---|---|
| CH₃OH | 33.400 | |
| IBA | 2.043 | |
| IBacid | 0.040 | |
| TEA | 3.600 | |
| HPA | 0.000 | |
| NPG | 59.232 | 99.36% |
| esters | 0.382 | |
| HNHP | 1.249 | |

IBA = isobutyl alcohol
IBacid = isobutyric acid
TEA = triethylamine
HPA = hydroxypivaldehyde
*NPG = neopentyl glycol
esters = e.g., neopentyl glycol monoformate, neopentyl glycol monoisobutyrate
HNHP = hydroxyneopentylhydroxypivalate
NPG purities calculated by GC on a "lights-free" (CH₃OH, IBA, TEA), "HNHP-free" basis.

EXAMPLE 8

Isobutyraldehyde (300.0 g, 4.16 mol), paraformaldehyde (131.51 g, 4.16 mol), and triethylamine (21.0 g, 0.21 mol) were charged with stirring into a 1L round-bottom flask fitted with a reflux condenser and equipped with an overhead stirrer. The charge was heated until a moderate isobutyraldehyde reflux was achieved. The slurry-phase reaction mixture became clear and homogeneous within 1.5h. The reaction was terminated when isobutyraldehyde reflux ceased. The clear, faintly yellowish aldol effluent was diluted in methanol to make a 30 wt. % aldol in methanol solution. The hydrogenation was performed by passing the methanolic aldol effluent upward through a fixed-bed of barium promoted $CuCr_2O_4$ at 130° C., 1.6 LHSV, and 2160 psig $H_2$ (>5:1 mole ratio $H_2$:HPA). Results follow:

| Components | Hydrogenated Solution (GC area %) | *Neopentyl Glycol Purity |
|---|---|---|
| CH₃OH | 59.877 | |
| IBA | 2.440 | |
| IBacid | 0.036 | |
| TEA | 2.359 | |
| HPA | 0.000 | |
| NPG | 34.442 | 99.26% |
| esters | 0.255 | |
| HNHP | 0.557 | |

IBA = isobutyl alcohol
IBacid = isobutyric acid
TEA = triethylamine
HPA = hydroxypivaldehyde
NPG = neopentyl glycol
esters = e.g., neopentyl glycol monoformate, neopentyl glycol monoisobutyrate
HNHP = hydroxyneopentylhydroxypivalate
*NPG purities calculated by GC on a "lights-free" (CH₃OH, IBA, TEA), "HNHP-free" basis.

EXAMPLE 9

Isobutyraldehyde (100.0 g, 1.39 mol), paraformaldehyde (49.1 g, 1.55 mol), and triethylamine (7.39 g, 0.069 mol) were charged with stirring into a 250 mL round-bottom flask fitted with a reflux condenser and equipped with a stirbar. The charge was heated until a moderate isobutyraldehyde reflux was achieved. The slurry-phase reaction mixture became clear and homogeneous within 1.25 h and was continued until isobutyraldehyde reflux ceased. The faintly yellowish reaction mixture was diluted in methanol to make a 10 wt. % aldol in methanol solution. The reduction was performed in a 2L autoclave reactor using 5.0 wt. % $CuCr_2O_4$ at 3000 psig $H_2$ for 1 h at 70° C. followed by 1 h at 130° C. Chromatographic analyses follow:

| Components | Hydrogenated Solution (GC area %) | *Neopentyl Glycol Purity |
|---|---|---|
| CH₃OH | 84.986 | |
| IBA | 1.018 | |
| IBacid | 0.012 | |
| TEA | 0.305 | |
| HPA | 0.000 | |
| NPG | 14.583 | **99.82% |
| esters | 0.026 | |
| HNHP | 0.050 | |

IBA = isobutyl alcohol
IBacid = isobutyric acid
TEA = triethylamine
HPA = hydroxypivaldehyde
NPG = neopentyl glycol
esters = e.g., neopentyl glycol monoformate, neopentyl glycol monoisobutyrate
HNHP = hydroxyneopentylhydroxypivalate
*NPG purities calculated by GC on a "lights-free" (CH₃OH, IBA, TEA), "HNHP-free" basis.
**A 10-tray fractional distillation gave 99.8% NPG product purity.

We claim:

1. Method of making neopentyl glycol comprising reacting isobutyraldehyde with paraformaldehyde to obtain a reaction product comprising hydroxypivaldehyde, forming a mixture of said reaction product with an alcohol of the formula RR'CHOH wherein R and R' are selected from the group consisting of hydrogen and alkyl groups having from one to five carbon atoms, said mixture comprising about 40% to about 90% alcohol, contacting said mixture with hydrogen in the presence of a hydrogenation catalyst, and recovering neopentyl glycol of at least about 99% purity.

2. Method of claim 1 wherein the reaction of isobutyraldehyde and paraformaldehyde is conducted in the presence of a catalyst comprising an amine of the formula $R^1R^2R^3N$ where $R^1$, $R^2$, and $R^3$ are selected from the group consisting of alkyl and aryl groups having one to 15 carbon toms and $R^1$ and $R^2$ optionally forms a substituted or unsubstituted cyclic group having about 5 to about 15 carbon atoms.

3. Method of claim 1 wherein the reaction of isobutyraldehyde and paraformaldehyde is conducted in the presence of a catalyst comprising one or more oxides of elements of Groups IB, IVA, IVB, VA, VB, VIB and VIII of the periodic table, together with a tertary amine.

4. Method of claim 1 wherein the alcohol comprises methanol.

5. Method of claim 1 wherein the alcohol is recovered prior to recovering the neopentyl glycol and is recycled.

6. Method of claim 1 wherein the hydrogenation catalyst comprises copper chromite.

7. Method of claim 1 wherein the hydrogenation reaction is conducted at a temperature of about 100° C. to about 200° C.

8. Method of claim 1 wherein the hydrogenation reaction is conducted at a pressure of about 500 psi to about 3000 psi.

9. Method of claim 1 wherein the reaction of isobutyraldehyde with paraformaldehyde employs a molar ratio of paraformaldehyde relative to the isobutyraldehyde of 0.5:1 to 2:1.

10. Method of claim 9 wherein the molar ratio of paraformaldehyde to isobutyraldehyde is about 1:1 to about 1.12:1.

11. Method of claim 1 wherein the neopentyl glycol is recovered by simple distillation.

12. Method of making neopentyl glycol comprising hydrogenating the reaction product of formaldehyde and isobutyraldehyde in the presence of at least about 40% of an alcohol of the formula RR'CHOH wherein R and R' are selected from the group consisting of hydrogen and alkyl groups having from one to five carbon atoms and no more than about 10% water based on the reaction product.

* * * * *

UNITED STATES PATENT AND TRADEMARK OFFICE
CERTIFICATE OF CORRECTION

PATENT NO. : 5,146,012
DATED : September 8, 1992
INVENTOR(S) : Salek et al

It is certified that error appears in the above-identified patent and that said Letters Patent is hereby corrected as shown below:

Column 8, line 10, after "Table IV", insert -- Example 5 --.

Column 9, line 22, change "*NPG = neopentyl glycol" to -- NPG = neopentyl glycol line 24, insert an asterisk -- * -- before "NPG purities".

Column 10, line 17, change "1.018" to -- 0.018 --;

line 49, claim 2, change "toms" to -- atoms --;

line 56, claim 3, change "tertary" to -- tertiary --.

Signed and Sealed this

First Day of February, 1994

Attest:

BRUCE LEHMAN

Attesting Officer    Commissioner of Patents and Trademarks